United States Patent
Horn

(10) Patent No.: US 6,908,745 B2
(45) Date of Patent: Jun. 21, 2005

(54) GAMMA STERILIZABLE CULTURE MEDIUM FOR THE IDENTIFICATION OF YEASTS AND FUNGI

(75) Inventor: Jürgen Horn, Egelsbach (DE)

(73) Assignee: Biotest AG, Dreieich (DE)

( * ) Notice: Subject to any disclaimer, the term of this patent is extended or adjusted under 35 U.S.C. 154(b) by 150 days.

(21) Appl. No.: 10/218,224

(22) Filed: Aug. 13, 2002

(65) Prior Publication Data
US 2003/0113834 A1 Jun. 19, 2003

(30) Foreign Application Priority Data
Aug. 14, 2001 (DE) .......................... 101 39 965

(51) Int. Cl.$^7$ ............................ C12Q 1/02; C12Q 1/04; C12Q 1/24; C12N 1/20

(52) U.S. Cl. .............................. 435/34; 435/29; 435/30; 435/253.6

(58) Field of Search .............................. 435/29, 30, 34, 435/253.6

(56) References Cited

U.S. PATENT DOCUMENTS

| 5,989,832 A | * | 11/1999 | Trias et al. ................... 435/7.2 |
| 6,060,474 A | * | 5/2000 | Williams et al. ........ 514/253.08 |
| 6,579,533 B1 | * | 6/2003 | Tormala et al. ............. 424/426 |
| 2002/0146397 A1 | * | 10/2002 | Hadden ................... 424/93.21 |

* cited by examiner

Primary Examiner—Herbert J. Lilling
(74) Attorney, Agent, or Firm—Norris McLaughlin & Marcus PA

(57) ABSTRACT

Gamma sterilizable culture medium for the selectively identification of yeasts and fungi with an addition of ciprofloxacin and, if necessary streptomycin or other antibiotics.

7 Claims, No Drawings

GAMMA STERILIZABLE CULTURE MEDIUM FOR THE IDENTIFICATION OF YEASTS AND FUNGI

The present invention relates to a gamma sterilizable culture medium for the identification of yeasts and fungi.

The media for selectively identifying yeasts and fungi contain antibiotics such as penicillin and streptomycin or chloramphenicol and chlortetracycline (Air Quality Monographs, Vol. 2, Elsevier Press 1994) to prevent the concurrent growth of bacteria. The addition of these antibiotics as well as a series of other antibiotics to a Sabouraud medium is described by McFaddin in Media for Isolation-Cultivation-Identification-Maintenance of Medical Bacteria, Williams & Wilkins, 1985.

In DP 19602345.9-41 is described the addition of sterile filtrated yeast extract to media, which can be additionally γ-sterilized and retain the growth characteristics of non-γ-sterilized media.

In the pharmaceuticals industry are sought γ-sterilized media for use in clean room areas and isolators. These clean room areas must be monitored for microbial contamination, and the product (that is, the microbiological nutrient medium) itself, with which this monitoring is carried out, should not introduce any contamination, but be sterile. The microbiological media are not completely sterile after autoclaving and filling into, for example, Petri dishes or other agar carriers, but have contamination rates in the order of magnitude of 0.1 to approx. 1%. Only as a result of an additional γ-sterilization (or β-sterilization) with high-energy radiation are killed the residual existing contaminations and a sterile product is obtained. However, many antibiotics are destroyed as a result of the γ-sterilization, so that afterward in selective media for yeasts and fungi whose selectivity is based on the addition of antibiotics, this selectivity no longer exists. In this way, for example, the antibacterial effect of chloramphenicol and chlortetracycline is completely destroyed as a result of a γ-radiation with 25 kGray and the antibacterial effect of the only still weakly effective penicillin is essentially reduced.

It is the object of the invention to find selective antibiotic additives, which inhibit the growth of concomitant flora also after a γ-sterilization without having a negative influence on the growth of yeasts and fungi.

This object is attained in accordance with the invention by adding ciprofloxacin or a combination of ciprofloxacin and streptomycin or, if necessary, a combination of ciprofloxacin and other antibiotics to the culture medium for the identification of yeasts and fungi. The range of the ciprofloxacin concentration lies therefore between 2 mg/l and 200 mg/l.

EXAMPLE 1

To a Sabouraud dextrose agar with a pH of 0.7 (Emmons Modification Difco Manual) are added after autoclaving 50 mg/l of ciprofloxacin and 50 mg of streptomycin in sterile-filtered form. Also 100 ml of a solution or raw, not autoclaved yeast extract, which was sterile-filtered at ambient temperature, are also added. The yeast extract is used with a suspension of 25 g/liter (2.5 g/100 ml) of yeast extract for sterile filtration as described in DP 196345.9. The agar is poured into Petri dishes or flexible plastic carriers (Biotest Surface Pathogen Indicator OKI or Biotest Aerial Pathogen Indicator LKI) and then γ-irradiated with 15–25 kGray.

EXAMPLE 2

To a Sabouraud dextrose agar with a pH of 7.0 (Emmons Modification, Difco Manual) are added 50 mg/l ciprofloxacin and the medium including the ciprofloxacin is autoclaved. After autoclaving is added a sterile-filtered yeast extract like in Example 1. Filling and γ-irradiation take place as in Example 1.

EXAMPLE 3

To a Sabouraud dextrose agar, like in Example 1, are added 50 mg/l of penicillin V and 50 mg/l of streptomycin (instead of ciprofloxacin and streptomycin) in sterile-filtered form. Filling and γ-irradiation take place as in Example 1.

EXAMPLE 4

To a Sabouraud dextrose agar, like in Example 1, are added 50 mg/l of chloramphenicol and 50 mg/l of chlortetracycline (instead of ciprofloxacin and streptomycin) in sterile-filtered form. Filling and γ-irradiation take place as in Example 1.

EXAMPLE 5

To a Sabouraud dextrose agar, like in Example 1, are added 15 mg/l of chloramphenicol and 15 mg/l of gentamycin (instead of ciprofloxacin and streptomycin) in sterile-filtered form. Filling and γ-irradiation take place as in Example 1.

EXAMPLE 6

A Rose Bengal agar of Difco is prepared according to the Difco Manual and 50 mg/l of sterile-filtered chloramphenicol are added. The filling takes place as in Example 1, but no additional γ-sterilization follows.

EXAMPLE 7

A Rose Bengal agar of Difco is prepared according to the Difco Manual and 50 mg/l of sterile-filtered streptomycin are added. The filling takes place as in Example 1, but no additional γ-sterilization follows.

EXAMPLE 8

A Sabouraud (Emmons Modification, Difco) is autoclaved according to the Difco Manual. Thereafter are added 50 mg/l of chloramphenicol and 50 mg/l of chlortetracycline. The medium is filled into plastic carriers (Biotest LKI), but is not γ-sterilized.

The culture media produced according to the preceding examples were examined as to their effectiveness against bacteria, yeasts and fungi. The results are summarized in Table 1. As can be seen therein, gram-positive pathogens (*B. subtilis, S. aureus*) are well inhibited by the medium 8, of the gram-negative pathogens (*E. coli, P. aeruginosa*), *P. aeruginosa* is inhibited only incompletely by medium 8, the medium according to the invention of Example 1 inhibits completely all the bacterial test pathogens, while the medium according to Example 4 (corresponds to Example 8, but in Example 4 with additional γ-irradiation) does no longer show an inhibition of any of the bacterial test pathogens.

On a selective nutrient medium for the growth of yeasts and fungi should grow only yeasts and fungi, but no bacteria. By means of the antibiotics in the unirradiated media according to Examples 5–8 are inhibited bacteria (except *P. aeruginosa*); fungi and yeasts show a good growth in Example 8, while in Example 6 and 7 Rose Bengal (prevents "spreading" in fungi and acts somewhat antibiotic) not all the fungi grow well. After γ-irradiation, only the media with ciprofloxacin according to Examples 1 and 2 still have the desired properties (no bacterial growth also with high injected pathogen counts, good growth of fungi and yeasts also with low pathogen counts). After the γ-irradiation (Examples 3–5), the media without ciprofloxacin have lost the desired properties and the bacterial flora are throughly intermingled. These desired properties are furthermore stable for a period of 7 months in the media containing ciprofloxacin, while even the unirradiated media according to Example 8 start losing their inhibiting effect on bacteria already after 3 months.

In further test series were examined the culture media according to Example 1, 4 and 8 as to their effectiveness as selective identification medium.

Aerial pathogen indicator strips (agar strips LKI of Biotest) are filled with medium according to Example 1 and Example 8. Thereafter, ten measurements per day are taken in one room on 5 consecutive days by using two aerial pathogen collection devices of the RCS Highflow type of Biotest. The measuring devices are mounted parallel at a 1 m distance and provided in a device with agar strips LKI with medium according to Example 8, the other with agar strips LKI with medium according to Example 1. At the same time, 600 l of air are collected for each. Thereafter, the position of the two devices is exchanged for the second measurement, etc. up to the tenth measurement. The strips are incubated at 22.5° C.±2.5° C. and the grown colonies are evaluated after three days. The colonies that do not show a typical fungus appearance are subjected to a gram staining and are microscopically evaluated to differentiate possible bacteria or yeast colonies. The yeasts are apportioned with the fungi, the bacteria are counted and collected separately.

The media according to Examples 1, 4 and 8 are also filled into Biotest Contact Slides. On unclean surfaces are carried out parallel imitations with these contact slides by using a surface pressure of 500 g per contact slide (use of a 500 g weight for weighing down the contact slide).

An evaluation similar to the aerial pathogen indicator strips is carried out after an incubation for three days at 22.5° C.±2.5° C.

The results which are summarized in Table 2 show that in the aerial pathogen measurements the medium 1 as well as the medium 8 prevent the growth of the bacterial concomitant flora. This is to be expected since mainly gram-positive pathogens occur as aerial pathogens, gram-negative pathogens are rarely isolated from the air (usually only under special conditions such as in animal pens, refuse separation plants, does it come to an isolation of gram-negative pathogens from the air).

Accordingly, with the medium according to the Example 1 in accordance with the invention, despite the γ-radiation after imitation, only fungi without bacterial contaminants are isolated as desired, while on the medium 8 numerous bacteria colonies are still thoroughly intermingled, and in the γ-irradiated version of medium 9 (this the medium of Example 4) the bacteria even grow predominantly. Therefore, the medium according to Example 1 γ-irradiated in accordance with the invention shows the same good yield of yeasts and fungi as a non-γ-irradiated standard medium on Sabouraud basis (Example 8) and a clearly better result than a non-γ-irradiated Rose Bengal medium according to Examples 6 and 7.

However, all the γ-irradiated Sabouraud media with standard antibiotics according to Examples 3–5 no longer inhibit the bacterial concomitant flora and are no longer selective. Only the use in accordance with the invention of ciprofloxacin, if necessary in combination with other antibiotics (Examples 1 and 2) inhibits also after γ-irradiation the concomitant flora with a simultaneously undiminished good growth of yeasts and fungi.

TABLE 1

| | | Growth on Agar according to: | | | | | | | |
|---|---|---|---|---|---|---|---|---|---|
| | Pathogen | Example 1 | Example 2 | Example 3 | Example 4 | Example 5 | Example 6 | Example 7 | Example 8 |
| Bacteria Inoculation $10^4$ pathogens and $10^3$ pathogens | E. coli ATCC8739 | no growth | no growth | good growth | good growth | growth | inhibited | inhibited | inhibited |
| | B. subtllis ATCC6633 | no growth | no growth | good growth | good growth | growth | inhibited | inhibited | inhibited |
| | S. aureus ATCC6538 | no growth | no growth | good growth | good growth | growth | inhibited | inhibited | inhibited |
| | P. aeruginosa ATCC9027 | no growth | no growth | good growth | good growth | growth | growth* | growth* | growth* |
| Yeasts 10-100 pathogens | C. albicans ATCC10231 | good growth | good growth | good growth | good growth | good growth | good growth | good growth | good growth |
| | S. cerevisia ATC9763 | good growth | good growth | good growth | good growth | good growth | little growth | little growth | good growth |
| Fungi Inoculation 10-100 pathogens | A. niger ATCC9642 | good growth | good growth | good growth | good growth | good growth | growth | growth | good growth |
| | C. herbarum DSMG3422 | growth | growth | growth | growth | growth | inhibited | inhibited | growth |
| | F. roseum DSM3019 | good growth | good growth | good growth | good growth | good growth | inhibited | inhibited | good growth |
| | M. racemosum ATCC42647 | good growth | good growth | good growth | good growth | good growth | good growth | good growth | good growth |
| | P. chrysogenum ATCC10106 | good growth | good growth | good growth | good growth | good growth | good growth | good growth | good growth |
| | S. chartarum ATCC16026 | growth | growth | growth | growth | growth | inhibited | inhibited | inhibited |
| | γ-irradiation | yes 25 kGray | yes 25 kGray | yes 25 kGray | yes 25 kGray | yes 25 kGray | no | no | no |

TABLE 1-continued

| Pathogen | Growth on Agar according to: Example 1 | Example 2 | Example 3 | Example 4 | Example 5 | Example 6 | Example 7 | Example 8 |
|---|---|---|---|---|---|---|---|---|
| Antibiotics used | cipro-floxacin + strepto-mycin | cipro-floxacin | penicillin V + strepto-mycin | chloram-phenicol + chlortetra-cycline | chloram phenicol + gentamycin | chloram-phenicol + Rose Bengal | strepto-mycin + Rosa Bengal | chloram-phenicol + chlortetra-cycline |

*Inoculation $10^3$ inhibited growth at $10^5$. After 3 months storage also growth of $10^3$.

TABLE 2

| Type of Measurement | Medium according to Example 8 | Medium according to Example 1 | Medium according to Example 4 |
|---|---|---|---|
| 5 × 10 measurements with 600 l each of air in parallel mounted RCS Highflow aerial pathogen collectors of Biotest | Overall 4022 fungi on 50 strips (= 100% yield) On average 80 per agar strip No bacterial contaminations | Overall 4384 fungi on 50 strips (= 109% yield with reference to the medium according to Ex. 8) on average 88 per agar strip No bacterial contaminations | Not carried out |
| 3 × 10 surface imitation of unclean surfaces parallel with medium according to Example 8 and Example 1 filled into Biotest Contact Slides | Overall 1587 fungi + 117 bacterial colonies | Overall 1692 fungi + 0 bacterial colonies | Overall 1076 fungi + 1468 bacterial colonies |

What is claimed is:

1. A gamma sterilized culture medium comprising an addition of ciprofloxacin wherein said culture medium selectively identifies yeasts and fungi.

2. Culture medium according to claim 1, wherein the concentration of ciprofloxacin in the medium amounts to 2 mg/l to 200 mg/l.

3. Culture medium according to claim 1, which additionally contains at least one other antibiotic besides ciprofloxacin.

4. Culture medium according to claim 3, wherein said other antibiotic is streptomycin.

5. Culture medium according to claim 2, which additionally contains at least one other antibiotic besides ciprofloxacin.

6. Culture medium according to claim 5, wherein said other antibiotic is streptomycin.

7. A method for determining the presence of fungi and yeast in air, said method comprising:

a) providing a culture medium according to claim 1;

b) exposing the culture medium to air;

c) incubating the culture medium for a period of time sufficient to grow fungi or yeast; and d) analyzing the culture medium for the growth of fungi or yeasts, wherein the growth or fungi or yeast indicates that the air contains fungi or yeast.

* * * * *